(12) United States Patent
Maahs (10) Patent No.: US 6,224,620 B1
(45) Date of Patent: *May 1, 2001

(54) DEVICES AND METHODS FOR PROTECTING A PATIENT FROM EMBOLIC MATERIAL DURING SURGERY (75) Inventor: Tracy D. Maahs, Redwood City, CA (US)

(73) Assignee: Embol-x, Inc., Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/443,581

(22) Filed: Nov. 18, 1999

Related U.S. Application Data (63) Continuation of application No. 09/181,790, filed on Oct. 28, 1998, now Pat. No. 6,051,015, which is a continuation of application No. 08/853,165, filed on May 8, 1997, now Pat. No. 5,846,260.

(51) Int. Cl.⁷ .................................................. A61M 29/00
(52) U.S. Cl. .............................................................. 606/200
(58) Field of Search .................................... 606/200, 191, 606/195, 198; 128/898; 604/96; 696/159

(56) References Cited

U.S. PATENT DOCUMENTS

| 3,923,065 | 12/1975 | Nozick et al. | 606/200 |
| 4,577,631 | 3/1986 | Kreamer | 606/200 |

(List continued on next page.)

FOREIGN PATENT DOCUMENTS

| 9301980 | 10/1993 | (BR) . |
| 3417738 A1 | 11/1985 | (DE) . |
| 0798134A1 | 2/1997 | (EP) . |
| 2567405 | 7/1984 | (FR) . |
| 764684 | 9/1980 | (SU) . |
| WO97/17100 | 5/1997 | (WO) . |

OTHER PUBLICATIONS

Barbut et al., "Cerebral Emboli Detected During Bypas Surgery Are Associated With Clamp Removal," *Stroke*, 25(12):2398–2402 (1994).

(List continued on next page.)

*Primary Examiner*—Michael H. Thaler
*Assistant Examiner*—Hoa B. Trinh
(74) *Attorney, Agent, or Firm*—Lyon & Lyon LLP (57) ABSTRACT A blood filter device and delivery system, comprising a tubular member with a filter. The tubular member includes a distal end adapted to enter an artery, and a port for receiving the filter. The filter includes a shaft having a handle on one end and an expandable filter device on the other end. The expandable filter device includes filter mesh and an expansion frame capable of assuming enlarged and contracted conditions. The shaft is removably received by the tubular member. The tubular member may be introduced into a blood vessel, and the expandable filter device may be deployed through the tubular member into the vessel. The expansion frame may be expanded to the enlarged condition to capture embolic material in the mesh, may be collapsed to the contracted condition, and may be removed from the vessel. The filter may be removed from the tubular member, and a new filter may then be received therein. Also described is a cannula having a proximal end, a distal end, and a lumen therebetween, the cannula further comprising a port disposed on an outer surface of the cannula for receiving a medical instrument, optionally a filter, for passage into the aorta or other suitable vessel.

15 Claims, 11 Drawing Sheets

U.S. PATENT DOCUMENTS

| | | | |
|---|---|---|---|
| 4,723,549 | 2/1988 | Wholey | 128/344 |
| 4,790,812 | 12/1988 | Hawkins, Jr. et al. | 604/22 |
| 4,873,978 | 10/1989 | Ginsburg | 128/345 |
| 4,919,133 | 4/1990 | Chiang | 606/159 |
| 4,921,484 | 5/1990 | Hillstead | 604/104 |
| 4,955,895 | 9/1990 | Sugiyama et al. | 606/194 |
| 5,053,008 | 10/1991 | Bajaj | 604/104 |
| 5,059,204 | 10/1991 | Lawson et al. | 606/171 |
| 5,147,371 | 9/1992 | Washington et al. | 606/127 |
| 5,330,451 | 7/1994 | Gabbay | 604/294 |
| 5,370,685 | 12/1994 | Stevens | 623/2 |
| 5,405,360 | 4/1995 | Tovey | 606/151 |
| 5,695,519 | 12/1997 | Summers et al. | 606/200 |
| 5,707,389 | 1/1998 | Louw et al. | 606/200 |
| 5,720,754 | 2/1998 | Middleman et al. | 606/127 |
| 5,814,064 | 9/1998 | Daniel et al. | 606/200 |
| 5,989,281 | * 11/1999 | Barbut et al. | 606/200 |
| 6,042,598 | * 3/2000 | Tsugita et al. | 606/200 |

OTHER PUBLICATIONS

Barbut et al., "Comparison of Transcranial Doppler Ultrasonography and Transesophageal Echocardiography to Monito Emboli During Coronary Artery Bypass Surgery," *Stroke* 27(1):87–90 (1996).

Barbut et al., "Aortic Atheromatosis and Risks of Cerebral Embolization," *Journal of Cardiothoracic and Vascular Anesthesia* 10(1):24–30 (1996).

van der Linden et al., "When Do Cerebral Emboli Appear During Open Heart Operations? A Transcrainial Doppler Study," *Ann. Thorac. Surg*. 551:237–241 (1991).

* cited by examiner

DEVICES AND METHODS FOR PROTECTING A PATIENT FROM EMBOLIC MATERIAL DURING SURGERY

This is a continuation of U.S. application Ser. No. 09/181,790, filed Oct. 28, 1998, now U.S. Pat. No. 6,051,015, which is a continuation of U.S. application Ser. No. 08/853,165, filed May 8, 1997, now U.S. Pat. No. 5,846,260. All of the above patents and applications are expressly incorporated herein by reference in their entirety.

SUMMARY

The present invention relates generally to blood filter devices for temporary placement in a blood vessel to capture embolic material, and more particularly to a cannula with a modular filter device for placement in a blood vessel to carry blood to the vessel and to entrap embolic material in the vessel, for example when delivering blood to the aorta from a bypass-oxygenator system during cardiac surgery. The present invention also relates to methods for protecting a patient from embolization which may be caused by procedures, such as incising, clamping and unclamping, which may dislodge atheromatous material from an artery.

BACKGROUND OF THE INVENTION

During cardiac surgery, it is often necessary to introduce a cannula into an artery or other blood vessel. For example, an arterial cannula is typically introduced into the aorta to deliver blood from a bypass-oxygenator system. Such a cannula generally includes a proximal end for receiving blood from a bypass-oxygenator machine, a distal end for entry into an artery, and a lumen extending between the proximal and distal ends.

One concern with such procedures is that calcified plaque or other embolic material may be dislodged, particularly when clamping or unclamping arteries such as the aorta. See Barbut et al., "Cerebral Emboli Detected During Bypass Surgery Are Associated With Clamp Removal," Stroke, 25(12):2398–2402 (1994), which is incorporated herein by reference in its entirety. Such embolic material may travel downstream, possibly becoming lodged in another portion of the blood vessel or possibly reaching a vital organ, such as the brain, where the material can cause substantial injury to the patient.

For this reason, some arterial cannulas may include a blood filter device attached directly to them. For example, an expandable filter device may be mounted on the distal end of a cannula, allowing the filter to capture any loose embolic material once the cannula is introduced into the vessel. Generally, such devices include an expandable frame, such as an inflation seal or an umbrella frame, and a filter mesh attached to the frame, the mesh being adapted to capture embolic material of a predetermined minimum size. The frame may be attached externally to the distal end, or alternatively, it may be retractably deployed from a lumen within the cannula.

The use of a cannula with such a filter device, however, may not be as effective as desired. For example, because the filter is generally attached to the distal end of the cannula, the filter may be exposed within the vessel for the entire duration of the procedure, sometimes several hours. Because of the length of time of most cardiac procedures, the filter mesh may eventually become clogged due to thrombus formation or buildup of embolic material, preventing the device from effectively capturing additional material and/or possibly impairing blood flow through the filter. If the filter is retractable, it may be closed within the vessel when it becomes clogged, but this prevents capture of embolic material throughout the remainder of the procedure.

Accordingly, there is a need for a filter device for use with an arterial cannula that minimizes the exposure of the filter within a blood vessel, thereby reducing the risk of clogging the filter mesh.

SUMMARY OF THE INVENTION

The present invention is directed to a modular blood filter device and a delivery system for intermittently introducing the filter device into a blood vessel during an extended surgical procedure, and to methods for using such a device. The present invention is also directed to an arterial cannula with modular filter device for temporary placement in a blood vessel to carry blood to the vessel and to entrap embolic material in the vessel, for example when delivering blood to the aorta from a bypass-oxygenator system during cardiac surgery.

Generally, an embodiment of an arterial cannula with modular filter device in accordance with the present invention comprises a cannula with a side port and a modular filter cartridge, the latter including an expandable filter device and a tubular cartridge. The cannula is an elongate tubular member, having a distal end adapted to enter an artery, a proximal end adapted to receive blood from a bypass-oxygenator machine, and a lumen which extends from the proximal end to the distal end. The cannula also includes a side port for receiving the modular filter cartridge. The side port may be attached to or integrally formed on the outer surface of the cannula, possibly on the front (downstream area), back (upstream area) or side of the cannula. Preferably, the side port is located adjacent the distal end of the cannula, for example above the suture flange thereon. More preferably, the side port extends diagonally from the outer surface to facilitate directing the filter device towards the distal end of the cannula. A passage extends front he side port to the lumen in the cannula, or alternatively, may extend distally from the side port along a wall of the cannula to an outlet on or adjacent the distal end of the cannula. The side port may include a hemostatic valve across the passage to provide a fluid-tight seal, yet allow a modular filter cartridge to be received in and removed from the side port.

An expandable filter device for use with embodiments of the present invention generally includes a semi-rigid shaft having a handle on its proximal end and an expansion frame on its distal end. Filter mesh is attached to the expansion frame to provide an expandable filter capable of assuming enlarged and contracted conditions.

The expansion frame for the expandable filter may be self-expanding upon deployment, or may be controlled from the handle on the proximal end of the shaft. For example, the expansion frame may be formed from a superelastic or shape memory material, such as a Nitinol ring, that opens automatically when deployed. Preferably, the ring includes kinks where the right is attached to the shaft, biasing the ring against the wall of a vessel, and maximizing the cross-section of the vessel intersected by the filter. Thus, once deployed, the ring automatically expands across the vessel, opening the filter, such as a substantially conical mesh, to capture embolic material in the vessel.

Alternatively, the expansion frame may include an annular inflation seal, such as a silicon balloon, that may be filled with fluid to open the mesh across the vessel into which the device is deployed. In this embodiment, the shaft may include an inflation lumen extending between the proximal and distal ends thereof for injecting and removing fluid.

The expansion frame may also be mechanically operated, such as by a guide wire and/or a spring connected to the expansion frame, generally controlled from the handle on the proximal end of the shaft. For example, the expansion frame may include a plurality of struts that may be biased to the contracted condition, possibly using a shape memory material or a spring. A ring attached to the struts may be directed axially to expand and contract the struts respectively between the enlarged and contracted conditions.

In addition, the cannula with modular filter device also includes a tubular cartridge into which the expandable filter device may be inserted. Generally, the cartridge is a tubular member providing a hemostatic seal between the shaft on the filter device and the side port on the cannula, or the cartridge may include a hemostatic valve to provide a fluid-tight seal between the cartridge and the filter device inserted therein. The cartridge generally has a shape similar to the side port, as well as the shaft on the filter device. Preferably, these components have similar cross-sections, such as a substantially square or rectangular shape, that limit the arterial cannula with modular filter device to a predetermined assembled orientation that ensures that the filter device is deployed across the vessel when deployed. The distal end of the shaft on the expandable filter device is generally inserted into the cartridge, such that the expansion frame and mesh are substantially contained within the cartridge, thereby providing a modular filter cartridge.

The modularity provided by the cartridge, combined with the side port on the cannula, is an important feature of the present invention. During use, the cannula may be introduced into a blood vessel, such as the aorta, using conventional procedures, a modular filter cartridge generally being provided in the side port prior to introduction of the cannula. Once the distal end of the cannula is in position within the vessel and the cannula is secured to the patient, the filter device may be deployed into the vessel. The shaft of the filter device is directed distally, causing the expandable filter on the distal end of the shaft to pass through the passage, through the lumen in the cannula and exit the distal end of the cannula into the vessel. The expansion frame may then expand automatically as it enters the vessel, or it may be expanded mechanically to its enlarged condition, opening the filter mesh substantially across the vessel and capturing any embolic material traveling therethrough. At any time, the expansion frame may be closed to its contracted condition, either automatically by withdrawing the expandable filter, or by mechanically closing it as described above, entrapping any embolic material captured by the mesh. The expandable filter may be returned into the cartridge by pulling the shaft proximally, and the modular filter cartridge may then be removed from the side port if desired. A new modular filter cartridge may be inserted into the side port, and a new filter may then be introduced into the vessel.

The ability to replace the filter at any time during a procedure is particularly useful in cardiac surgery. For example, the cannula and filter may be deployed as described above within the aorta. The aorta may then be clamped in preparation for a bypass procedure, possibly dislodging embolic material from the wall of the aorta and traveling downstream. With the filter deployed, however, embolic material released during this action may easily be captured by the filter device. Once the aorta is clamped, the risk of embolic material breaking loose is substantially reduced, and so the filter may be removed without substantial concern about embolic material escaping to other areas of the patient.

Later in the surgery, a new filter may be introduced into the aorta when the risk of embolic material becoming dislodged is again increased, as for example when the aorta is unclamped. Because a new filter may be deployed, any embolic material that is dislodged has a much greater likelihood of being captured by the filter without substantially impairing blood flow through the vessel. Thus, a cannula with modular filter device in accordance with the present invention may more effectively capture and remove embolic material released during extended procedures, such as coronary bypass surgery.

Accordingly, a principal object of the present invention is to provide a modular blood filter device and delivery system that allows the filter to be decoupled from the delivery system when not needed, and that allows a new filter to be introduced to more effectively capture embolic material within the vessel, such as during an extended surgical procedure.

It is also an object of the present invention to provide an arterial cannula with modular filter device that substantially minimizes the likelihood of the blood filter becoming clogged and ineffective during use.

DRAWINGS

Additional objects and features of the present invention will become apparent from consideration of the following description taken in conjunction with the accompanying drawings.

DETAILED DESCRIPTION OF THE INVENTION

Figure 16:
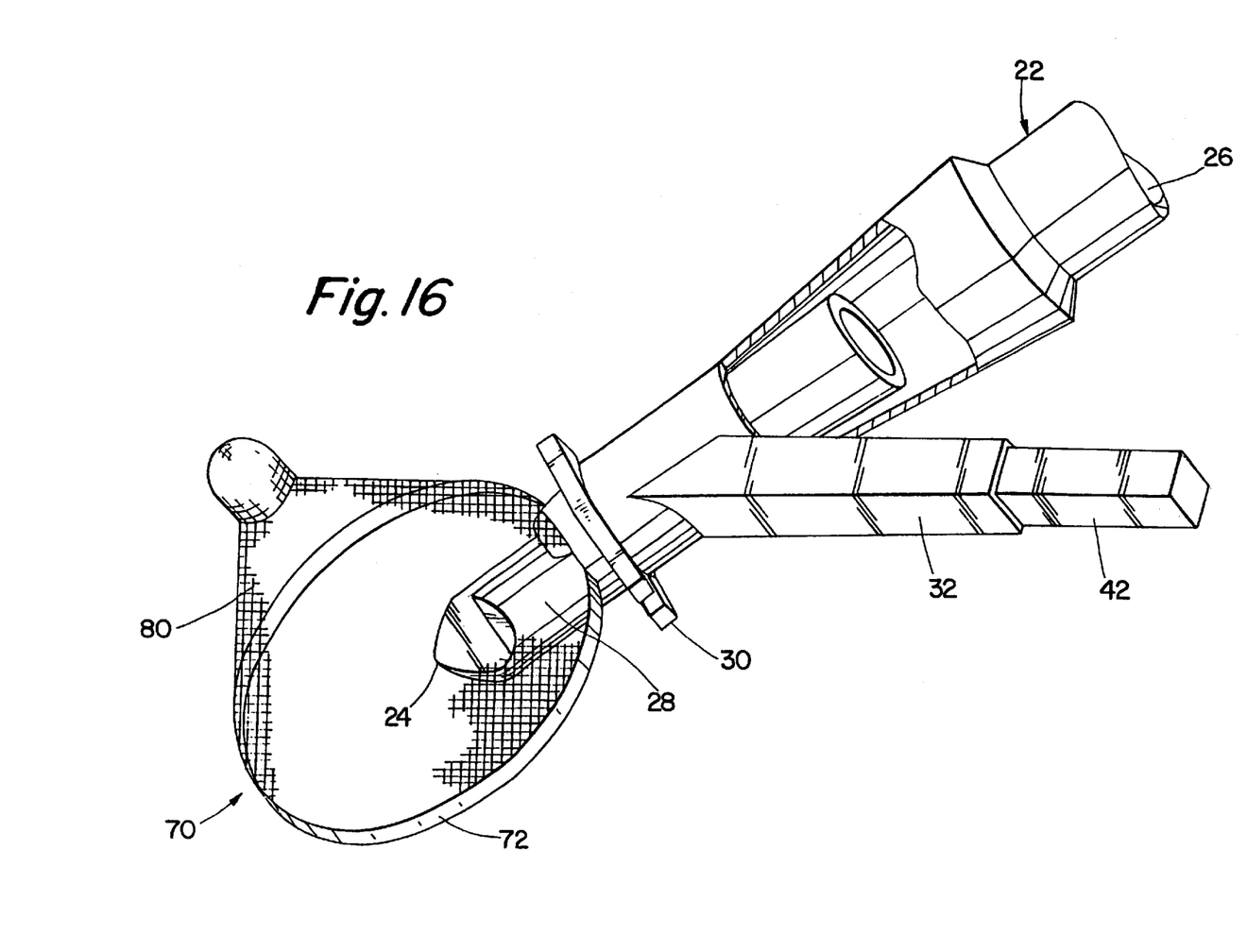
FIGS. 16 and 17 are perspective views of the distal portion of a cannula with modular filter device in accordance with the present invention, with the expandable filter device deployed.
Figure 17:
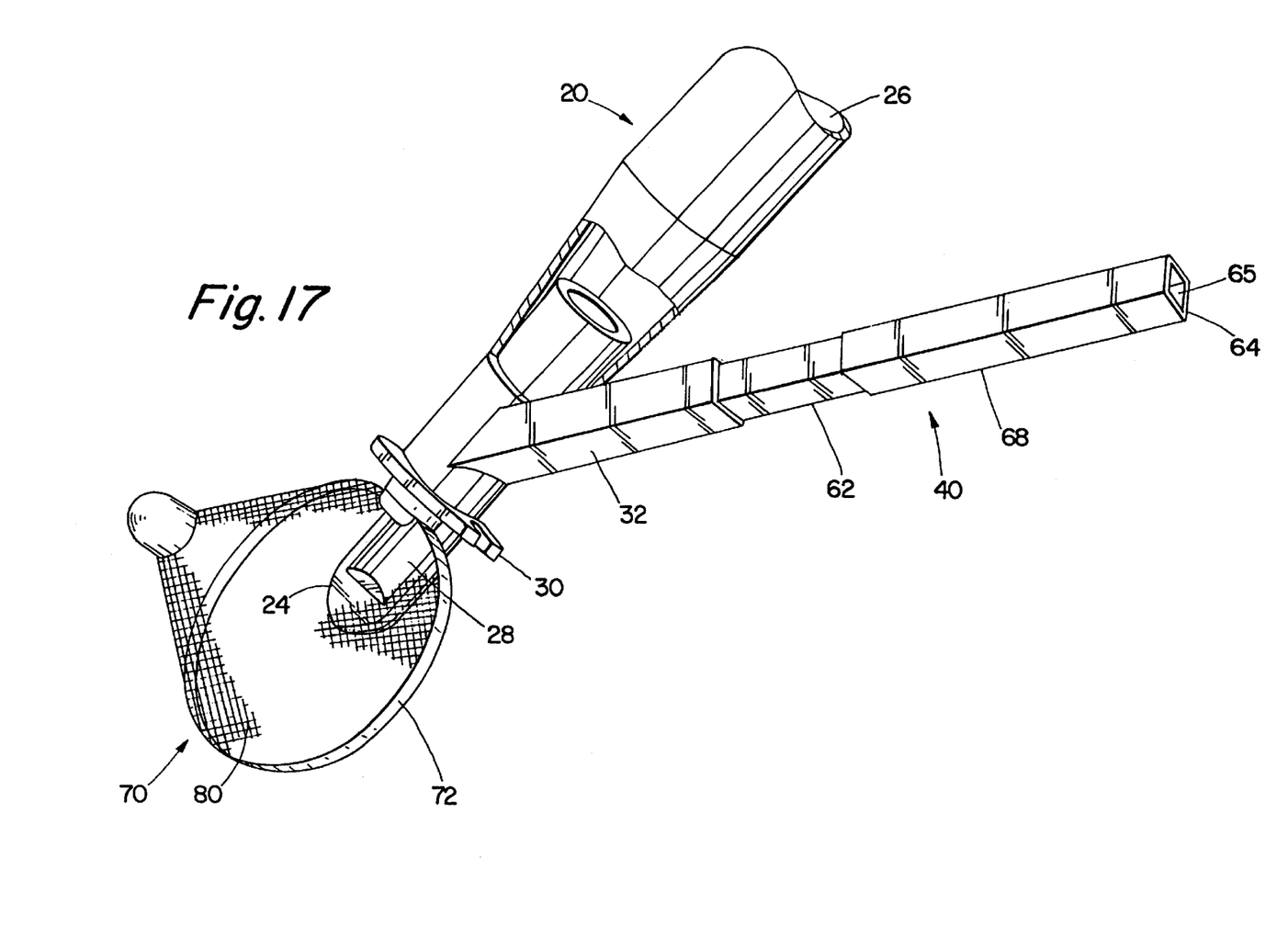
Figure 18:
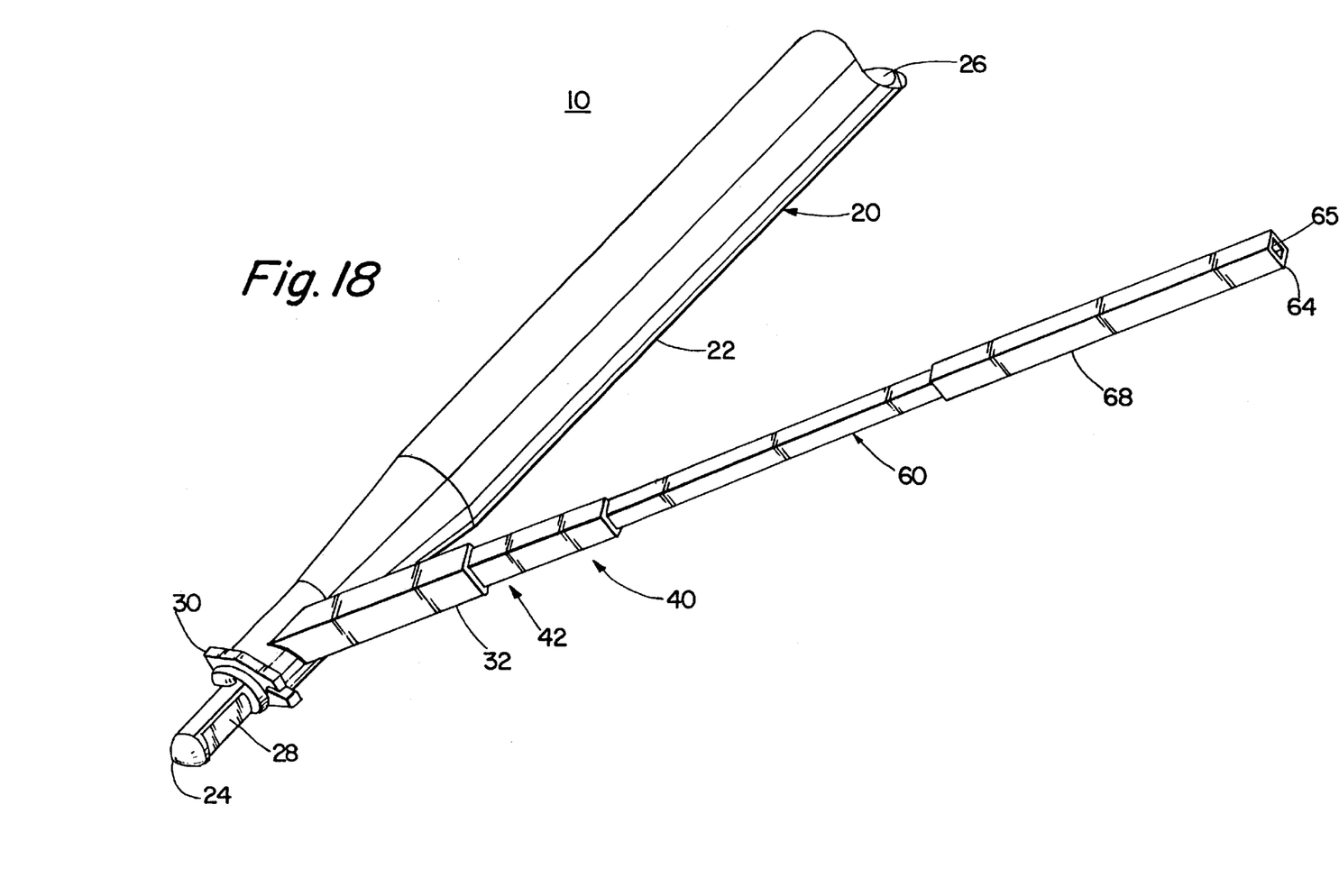
FIG. 18 is a perspective view of a distal portion of an arterial cannula with modular filter device, showing the modular filter cartridge after being received in the arterial cannula.
Figure 19:
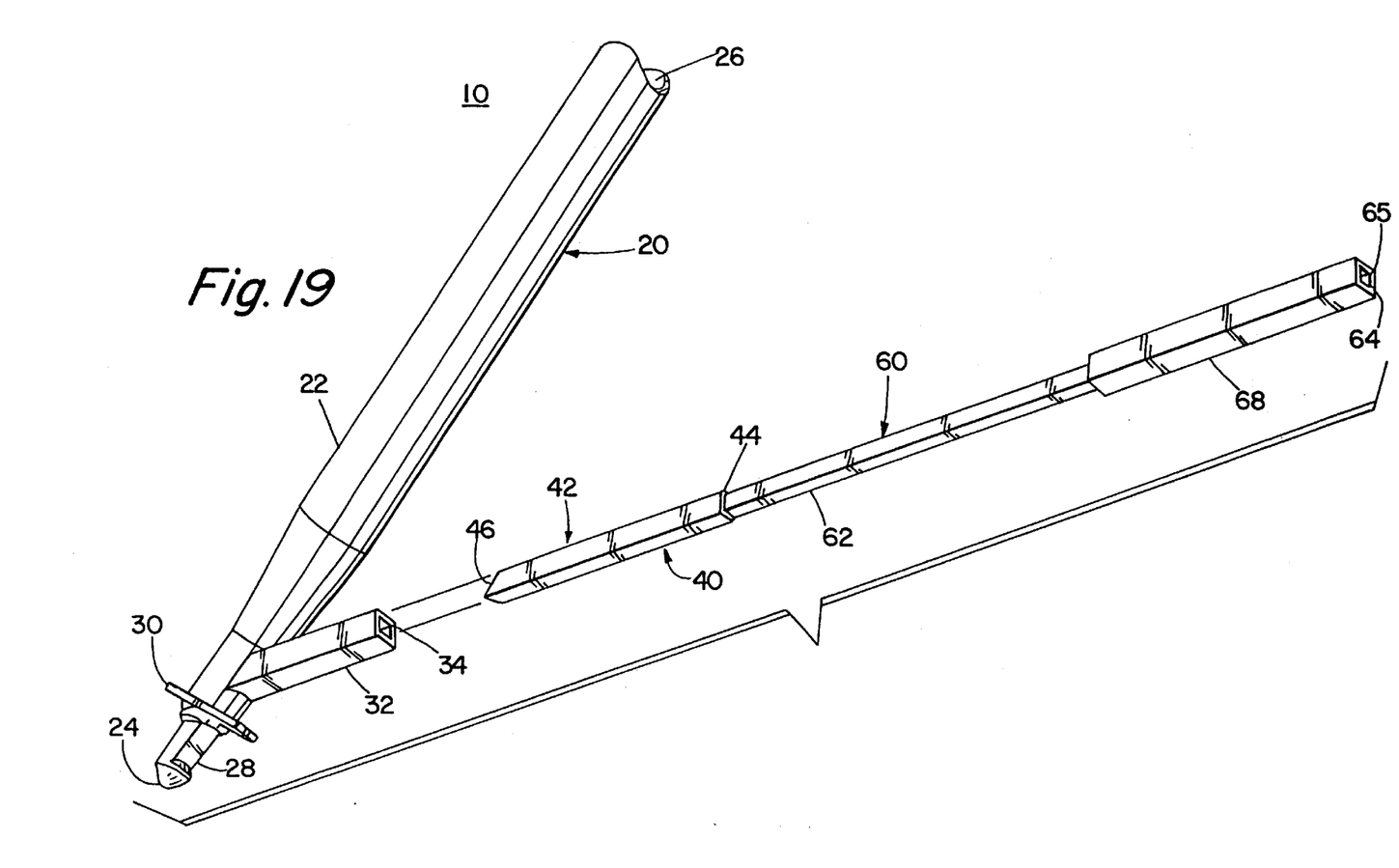
FIG. 19 is a perspective view of a distal portion of the arterial cannula with modular filter device of FIG. 18, prior to the modular filter cartridge being received in the arterial cannula.

Turning now to the drawings, FIGS. 1–5 and 16–19 show embodiments of an arterial cannula with modular filter device 10 in accordance with the present invention. As shown in FIGS. 18 and 19, the device 10 generally includes three components, namely a cannula 20, a tubular cartridge 42 and an expandable filter device 60, the latter two components together defining a modular filter cartridge 40.

The cannula 20 is an elongate tubular member 22, having a proximal end (not shown), a distal end 24, and a lumen 26 which extends between the proximal and distal ends 24. The proximal end is adapted for receiving blood from a bypass-oxygenator machine (not shown). The distal end 24 has a tapered, curved and/or rounded end adapted to enter an artery (not shown), and includes an outlet 28 communicating with the lumen 26. The cannula 20 may be formed from a substantially rigid material.

Figures 1, 2:
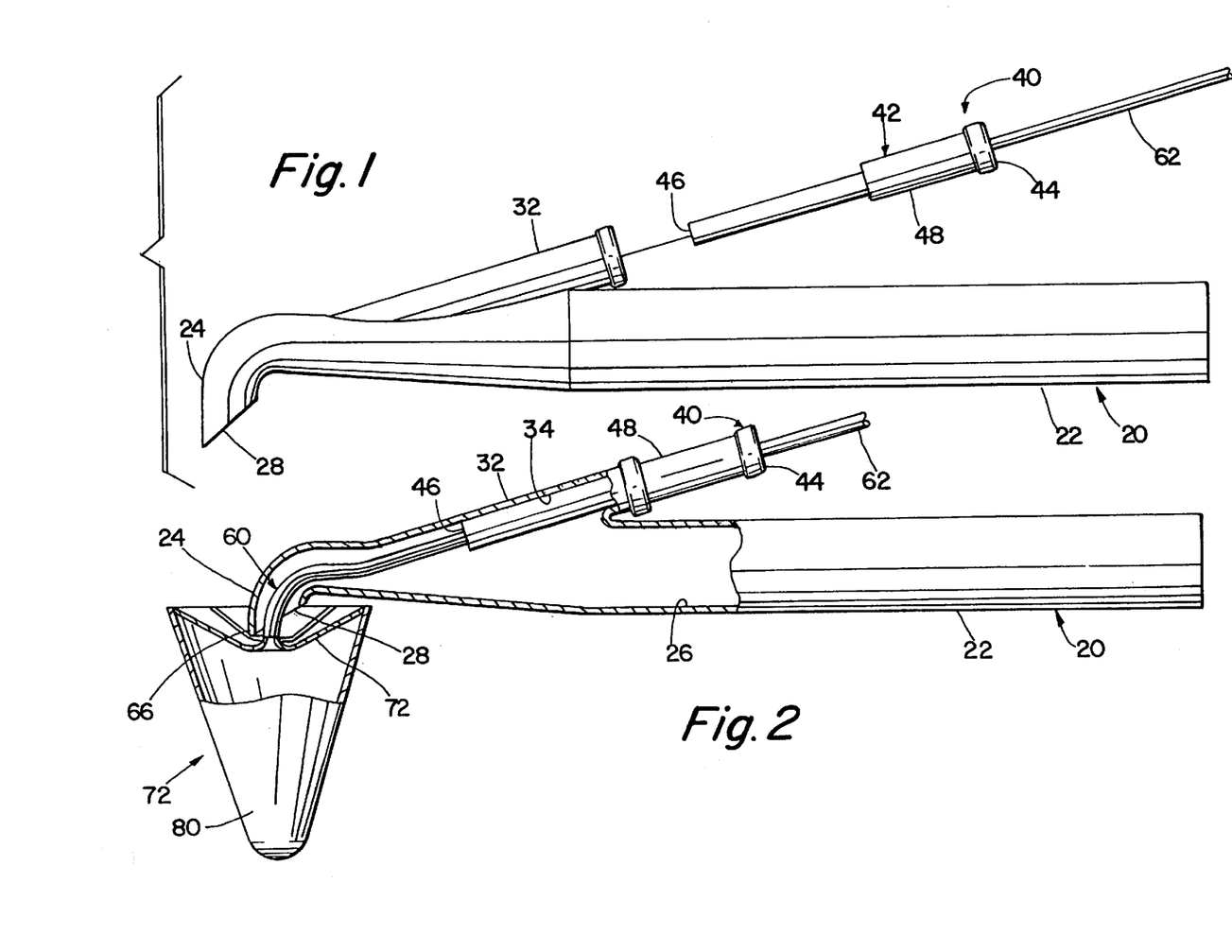
FIG. 1 is a side view of an embodiment of an arterial cannula receiving a modular filter cartridge therein.
FIG. 2 is a partially cut-away side view of the arterial cannula of FIG. 1 with the modular filter cartridge received therein, showing the filter partially deployed.
Figure 3:
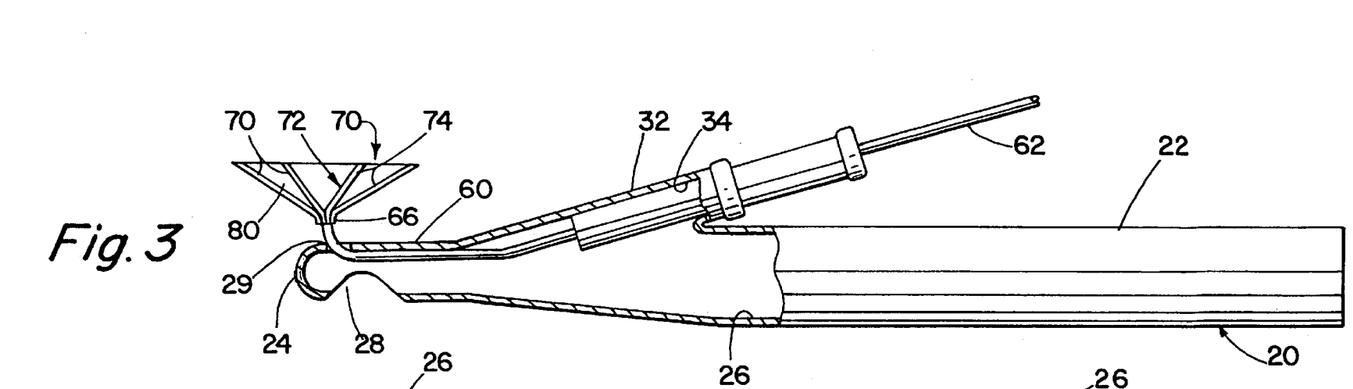
FIG. 3 is another partially cut-away side view of another preferred embodiment of an arterial cannula with the modular filter cartridge received therein, showing an alternative arrangement of the deployed filter.

The cannula 20 includes a side port 32 for receiving the modular filter cartridge 40. The side port 32 may be attached to or integrally formed on the cannula 20, possibly on the front (downstream area), back (upstream area) or side of the cannula, as shown, for example, in FIGS. 4 and 5. Preferably, the side port 32 is located adjacent the distal end 24 of the cannula 20 above a suture flange 30 thereon, and extends diagonally from the cannula 20. A passage 34 extends from the side port 32 to the lumen 26 in the cannula 20, as shown in FIG. 2. Alternatively, the passage 34 may communicate with the lumen 26 of the cannula 20, and the distal end 24 of the cannula 20 may include a separate filter outlet 29, as shown in FIG. 3, or the passage 34 may be isolated from the lumen 26 and extend distally from the side port 32 along a wall of the cannula 20 to a filter outlet (not shown) on or adjacent the distal end 24 of the cannula 20. Preferably, the side port 32 also has a predetermined cross-sectional configuration corresponding to the modular filter cartridge 40, as explained below. Optionally, the side port 32 may include a hemostatic valve (not shown) across the passage 34, providing a fluid-tight seal that prevents fluid flow out of the passage 34 from the lumen 26 of the cannula 20, yet allows the modular filter cartridge 40 to be received in and removed from the side port 32.

The tubular cartridge 42 is generally an elongate tubular member having a proximal end 44, a distal end 46 and a channel (not shown) for receiving the filter device 60. The cartridge 42 facilitates the modular nature of the device 10, providing a hemostatic seal between the filter device 60 and the side port 32 on the cannula 20. The cartridge 42 may have an outer wall 48 shaped similarly to the passage 34 in the side port 32 as shown in FIGS. 18 and 19, thereby providing a fluid-tight seal when the modular filter cartridge 40 is received in the side port 32. The channel in the cartridge 42 may also have a shape similar to the filter device 60 to provide a fluid-tight seal between the cartridge 42 and the filter device 60. Alternatively, a hemostatic valve (not shown) may be provided across the channel, for example at the proximal end 44 of the cartridge 42 to provide a fluid-tight seal, yet allow the filter device 60 to be slideably received in and possibly removed from the cartridge 42. Preferably, the cartridge 42 is provided from molded plastic materials that provide a hemostatic seal when the outer wall 48 of the cartridge 42 slideably engages the passage 34 in the side port 32, and when the shaft 62 of the filter device 60 slideably engages the channel in the cartridge 42.

Referring to FIGS. 16–19, the expandable filter device 60 generally includes a shaft 62, a handle 68 and an expandable filter 70. The shaft 62 is generally an elongate member, having the handle 68 on its proximal end 64 and the expandable filter 70 on its distal end 66. Optionally, the shaft 62 may include a passage 65, such as for an inflation lumen or a mechanical control apparatus for the expandable filter 70, extending between the proximal end 64 and the distal end (not shown). The shaft 62 may be provided from a resilient semi-rigid material that is biased to a particular shape, for example to remain substantially straight, but is sufficiently flexible to follow the contour of the passage 34 and/or the lumen 26 in the cannula 20. Exemplary materials include plastic or metal. Generally, the shaft 62 may have a cross-section corresponding to the channel in the cartridge 42, thereby providing a hemostatic seal that prevents flow of fluid through the channel, although alternatively, the cartridge 42 may include a separate seal as described above, or the shaft 62 may include a seal (not shown).

Preferably, the cross-sections of the side port 32, the cartridge 42 and the shaft 62 have a substantially square, rectangular or other similar shape. The corresponding shape preferably limits the device 10 to being assembled in a single orientation. This may be particularly important to ensure that the expandable filter 70 is deployed within a blood vessel such that it intersects the vessel, and substantially engages the wall of the vessel to effectively capture embolic material. The side port 32 also helps orient the surgeon using the device 10 with respect to the vessel. For example, with the side port 32 on the side of the cannula 20 as shown in FIGS. 16 and 17, the surgeon may orient the side port 32 perpendicular to the vessel to ensure that the outlet is directed downstream and that the filter is oriented for proper deployment.

Figure 8:
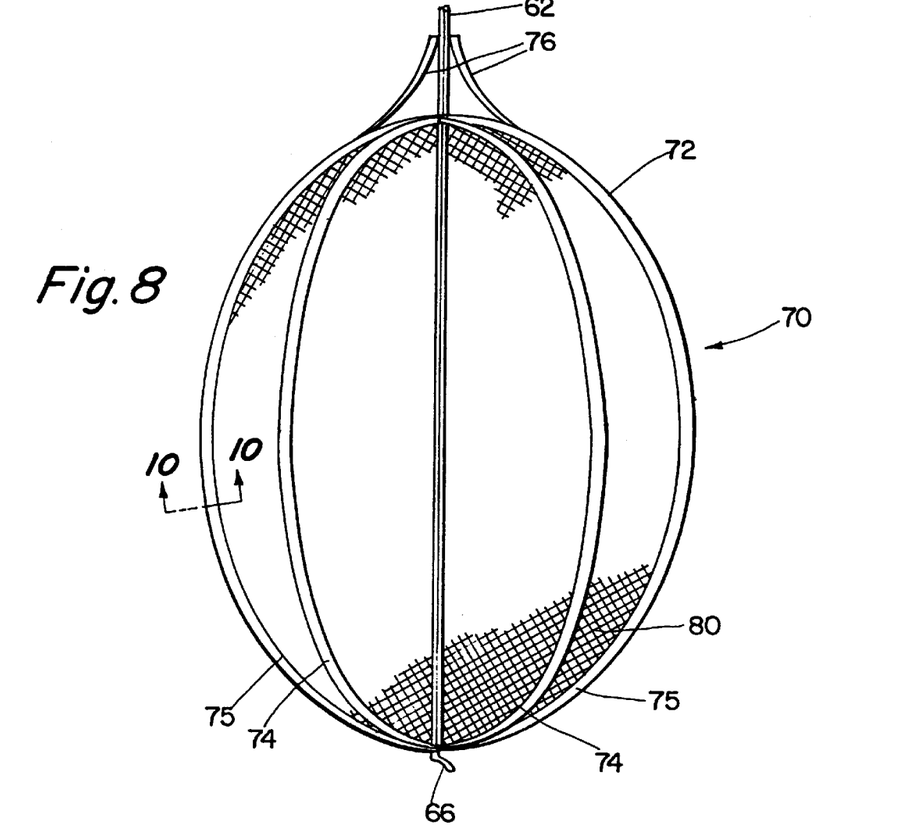
FIG. 8 is a back view of an embodiment of an expandable filter device in accordance with the present invention.
Figure 9:
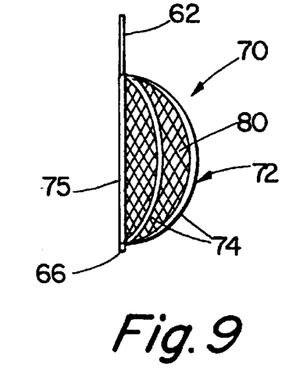
FIG. 9 is a side view of the expandable filter device of FIG. 8.

Turning now to FIGS. 8 and 9, an embodiment of an expandable filter 70 is shown that may be provided on or near the distal end 66 of the shaft 62. The expandable filter 70 generally includes an expansion frame 72 capable of assuming enlarged and contracted conditions, and filter mesh 80. Preferably, the expansion frame 72 includes a plurality of struts 74 that may be expanded and contracted to define respectively the enlarged and contracted conditions. Filter mesh 80 is attached to the struts 74, 75 of the expansion frame 72. For a complete explanation of the design and construction of a filter mesh for use in accordance with the present invention, the reader is referred to Barbut et al., U.S. application Ser. No. 08/553,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. application Ser. No. 08/640,015, filed Apr. 30, 1996, Barbut et al., U.S. application Ser. No. 08/645,762, filed May 14, 1996, and Lyon & Lyon, filed Apr. 16, 1997. The disclosure of these references and any others cited herein are expressly incorporated herein by reference.

In the preferred embodiment of FIGS. 8 and 9, the struts 74, 75 may open automatically into a substantially hemispherical shape when deployed, for example, by providing them from plastic, spring stainless steel, or a superelastic and/or shape memory material, such as Nitinol, that is biased to expand to define the hemispherical shape. Stabilizers 76 may be provided to stabilize the expansion frame 72, or may be omitted if the bias of the struts 74, 75 provides sufficient stability. In addition, the struts 74, 75 may be attached to the shaft 62 using hinged joints to facilitate expanding and contracting the expansion frame 72.

Figure 10:
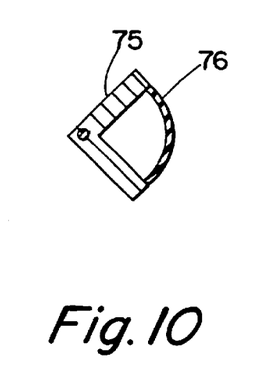
FIG. 10 is a cross-section of a support strut taken along line 10—10 of FIG. 9, including an inflation seal for engaging the wall of a vessel when the expandable filter device is deployed.
Figure 11:
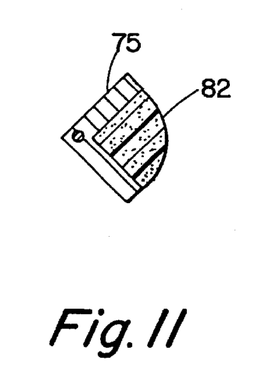
FIG. 11 is a cross-section of an alternative embodiment of a support strut taken along line 10—10 of FIG. 9, including a self-expanding foam for engaging the wall of a vessel.

The open end struts 75 may also include seals for engaging the wall of a blood vessel to substantially minimize embolic material traveling around the periphery of the deployed expandable filter 70. For example, as shown in FIG. 10, the struts 75 may include a silicone or urethane balloon 76 attached along their length that may be inflated from a lumen (not shown) extending between the struts 75 and the shaft 62. The balloon 76 may also be used to expand the expansion frame 72 to its enlarged condition if the struts 74, 75 are unbiased or are biased to the contracted condition. Alternatively, as shown in FIG. 11, the struts 75 may include a selfexpanding foam 82, such as silicone, that will expand when the expandable filter 70 is deployed to substantially engage the wall of the vessel.

Alternatively, as shown in FIG. 3, the struts 74 may have an umbrella-like configuration, which may be particularly useful when the expandable filter 70 is deployed out a filter outlet 29 on the back (upstream side) of the cannula 20. The struts 74 may be biased to expand to the enlarged condition. To remove the expandable filter 70, the shaft 62 may be pulled proximally, closing the struts 74 as they enter the filter outlet 29.

Figure 6:
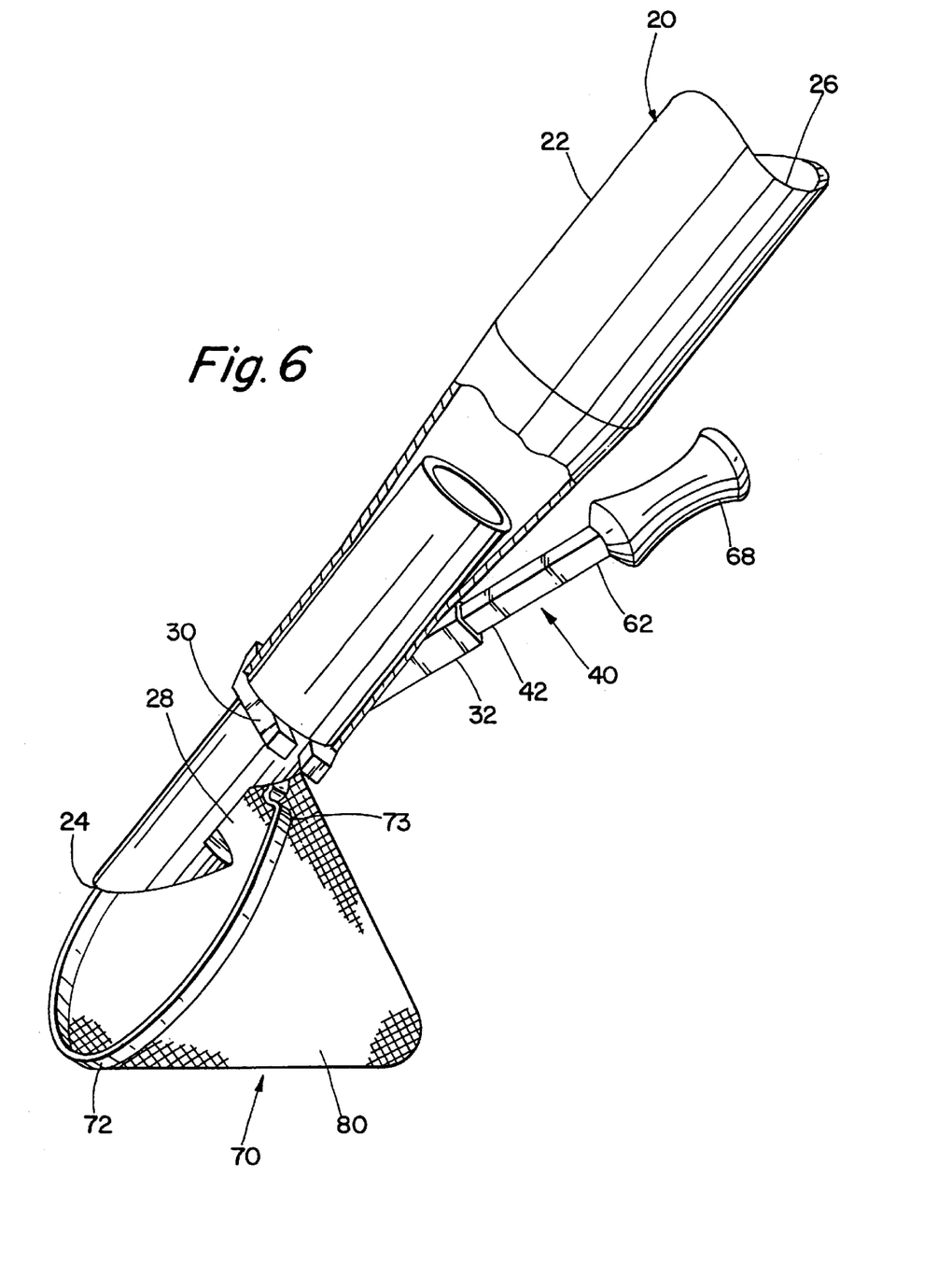
FIG. 6 is a perspective view of a distal portion of an arterial canlula from a generally upstream position, showing a conical filter device fully deployed.
Figure 7:
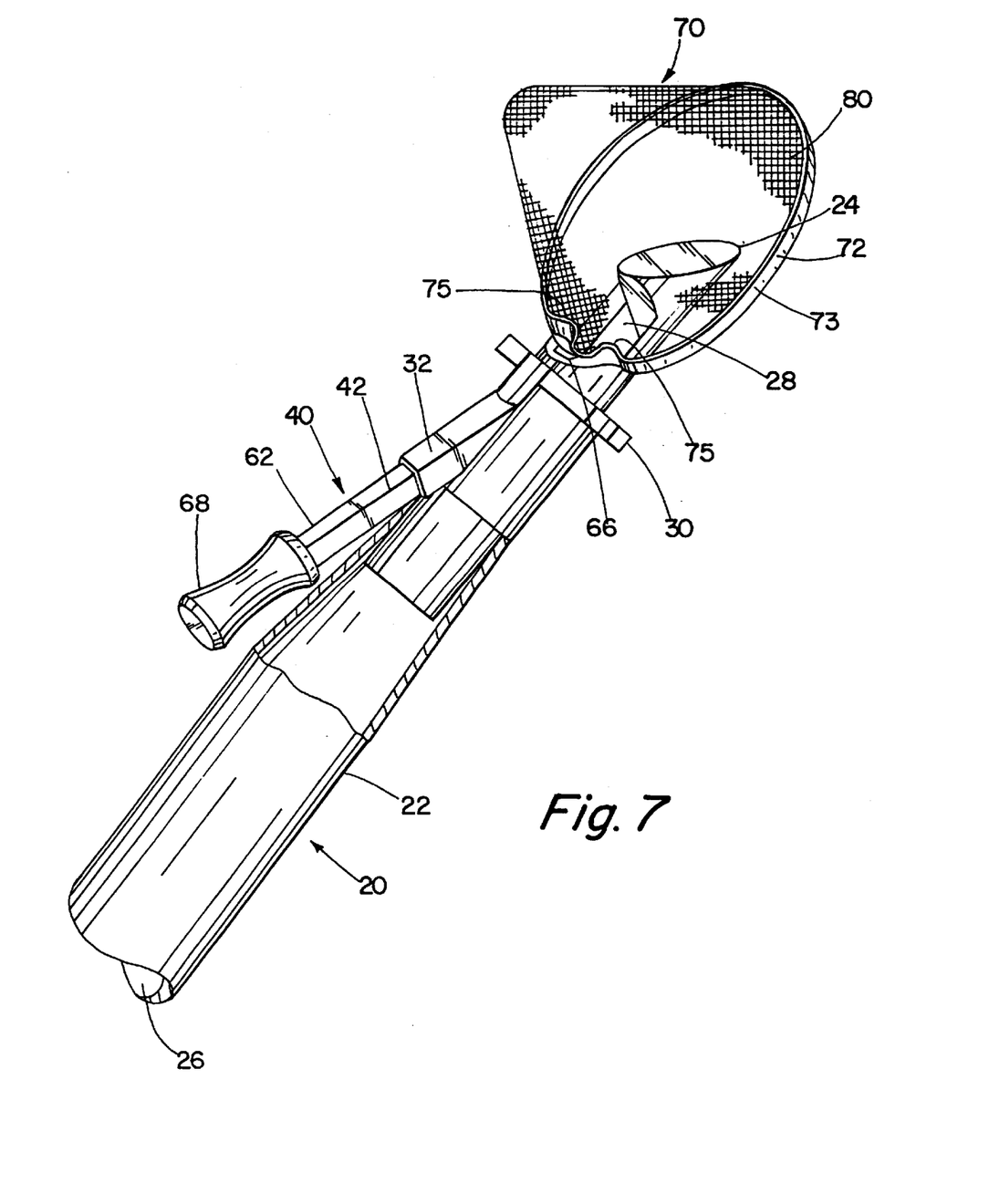
FIG. 7 is a perspective view of the distal end of the arterial cannula of FIG. 6 from a generally downstream position.

In another preferred embodiment, such as that shown in FIGS. 6 and 7, the expansion frame 72 is a self-expanding ring 73 formed from spring stainless steel or a superelastic and/or shape memory material, such as Nitinol. The ring 73 may be compressed for insertion into the cartridge 42, but, because of the shape memory of the material, it is biased to open automatically into an annular shape when the expandable filter 70 is deployed. Preferably, the ring 73 also includes a kink 75 adjacent the distal end 66 of the shaft 62 to bias the ring 73 against the wall of the vessel, and maximize the cross-section of the vessel intersected by the expandable filter 70. Without the kink 75, the ring may deform slightly, creating an imperfect circular cross-section that may allow embolic material to escape around the periphery of the deployed expandable filter 70. The filter mesh 80 attached to the ring 75 preferably has a substantially conical shape, such that when the ring 75 expands across the vessel, the mesh 80 is pulled open downstream by blood flow in the vessel to capture any embolic material traveling through the vessel.

Figure 15:
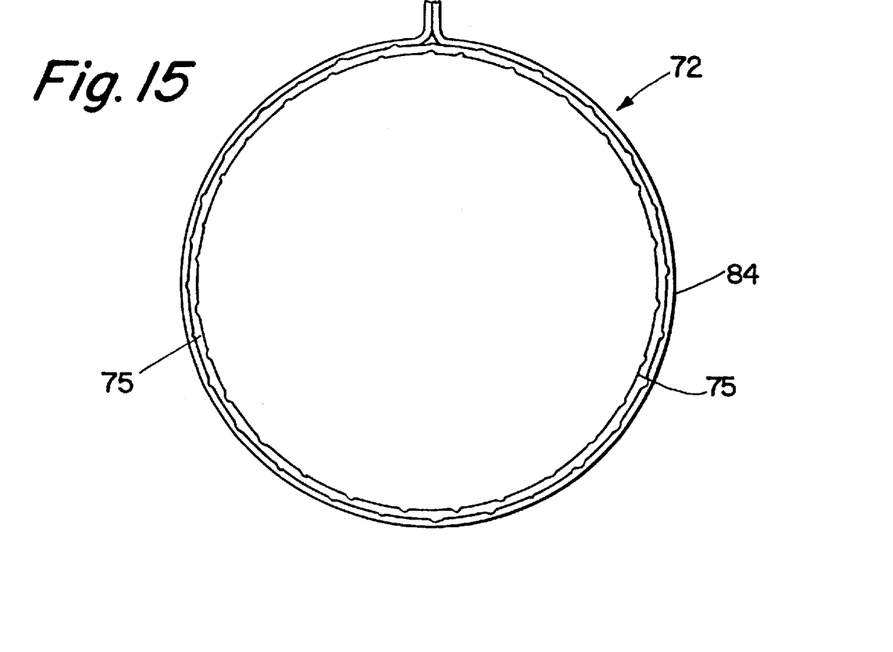
FIG. 15 is a side view of an embodiment of an expansion frame having "sausage" struts and an inflation seal.

Alternatively, as shown in FIG. 15, the expansion frame 72 may include a ring 75 having a "sausage" configuration, that is, having hinges or dimples on several locations around the ring 75, allowing the ring 75 to enlarge and contract more easily, and conform tightly to vessel lumen topography. Preferably, this embodiment also includes a balloon 84 attached around the periphery of the ring 75 to guide the ring 75 to assume a substantially round configuration when the balloon 82 is inflated.

Figure 12:
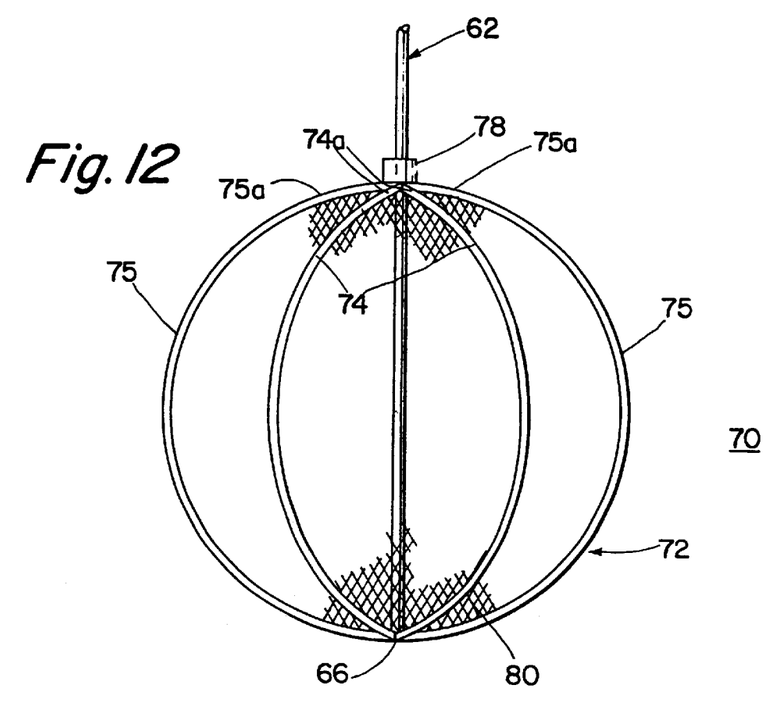
FIGS. 12 and 13 are side views of alternative embodiments of expansion frames for use in an expandable filter device in accordance with the present invention.
Figure 13:
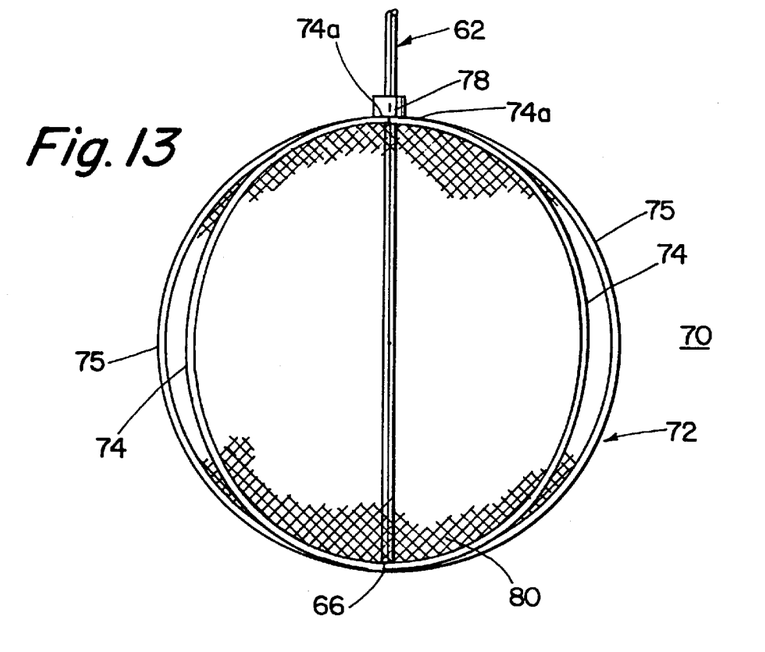

In still another preferred embodiment, a mechanically-operated expansion frame 72 may be provided. For example, the expansion frame 72 of FIGS. 12 and 13 includes a ring 78 to which one end 74a, 75a of the struts 74, 75 are attached. The ring 78 may be slideable axially in relation to the shaft 62, for example by use of a control wire or sleeve (not shown) to expand and contract the struts 74, 75. Alternatively, the ring 78 may be twisted radially to open and/or close the struts 74, 75.

Figure 14:
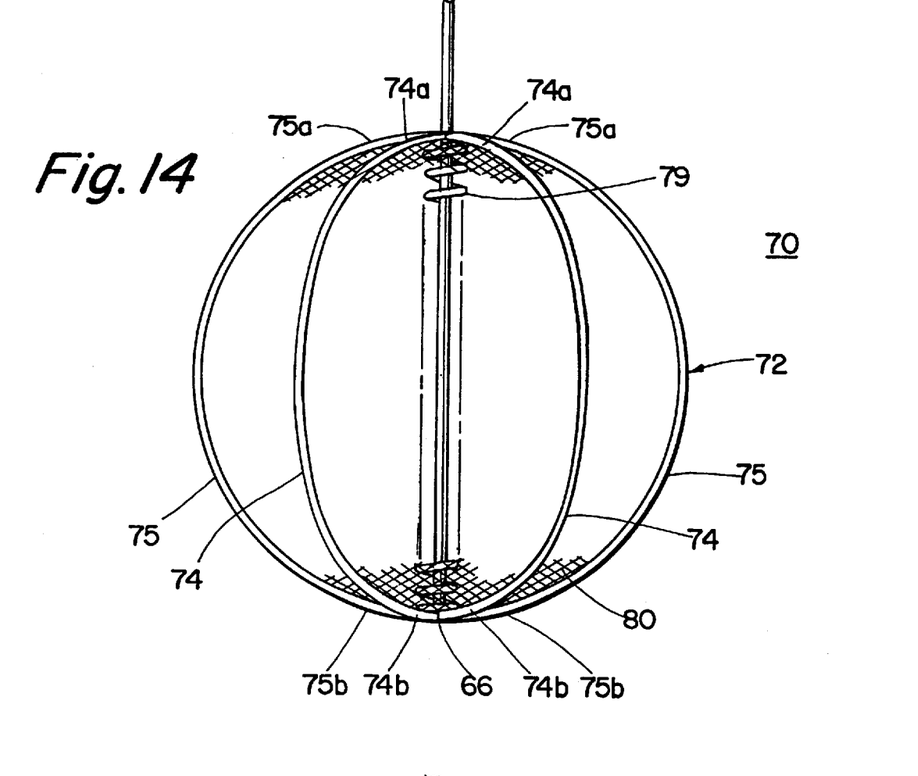
FIG. 14 is a side view of a spring-activated expansion frame for an expandable filter device in accordance with the present invention.

As shown in FIG. 14, a spring 79 may be provided between the ends 74a, 75a, 74b, 75b of the struts 74, 75. The spring 79 may be compressed by use of a control wire or like apparatus (not shown) to expand the struts 74, 75 to the enlarged condition. When the filter 70 is to be removed, the spring 79 biases the expansion frame 72 to compress the struts 74, 75 to the contracted condition, entrapping embolic material in the mesh 80.

Alternatively, the open end struts 75 may themselves be provided from compressed springs (not shown), thus biasing them to the contracted condition. Such struts may conform more easily to the shape of the wall of the vessel than solid struts.

Generally, as shown in FIG. 19, the cannula 20 and the modular filter device 40 are furnished separately, although alternatively, the device 10 may be provided preassembled as in FIG. 18. The cartridge 42 and filter device 60, however, are generally preassembled, thereby providing the modular filter cartridge 40. This is accomplished by compressing the expandable filter (not shown) and directing the distal end (not shown) of the shaft 62 into the channel (not shown) in the cartridge 42, such that the expansion frame and mesh (not shown) are substantially contained within the cartridge 42.

Figure 4:
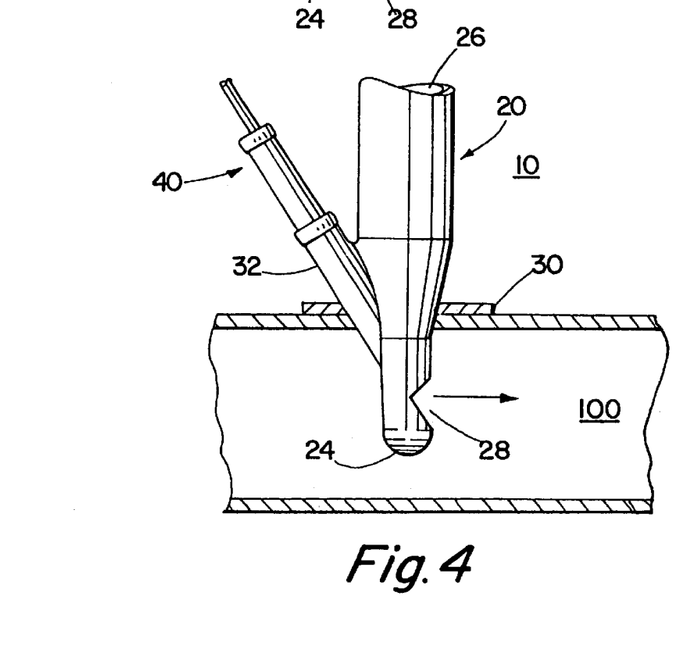
FIGS. 4 and 5 are side views of the distal end of an arterial cannula in accordance with the present invention introduced into a blood vessel, showing the side port located on the back and on the front, respectively, of the cannula.
Figure 5:
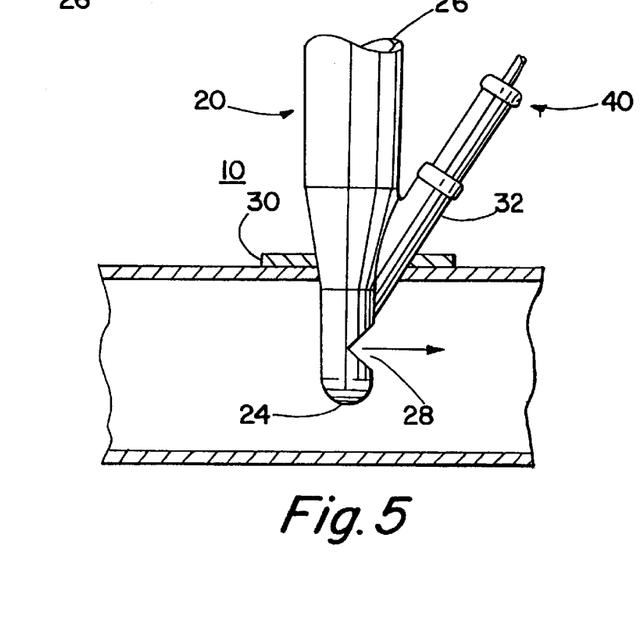

Prior to use, the modular filter cartridge 40 may be inserted into the side port 32 of the cannula 20, as shown in FIG. 18. The distal end 24 of the cannula 20 may then be introduced into a blood vessel 100, such as the aorta, using conventional procedures, as illustrated in FIGS. 4 and 5, allowing blood to be carried into the vessel 100 from the lumen 26. Once the distal end 24 of the cannula 20 is in position within the vessel 100 and the cannula 20 is secured to the patient, such as using the suture flange 30, the expandable filter may be deployed into the vessel, as shown in FIGS. 16 and 17.

As shown in FIGS. 2 and 3, the shaft 62 of the filter device 60 may be directed distally to deploy the expandable filter 70 on its distal end 66. This causes the expandable filter 70 to pass through the passage 34, through the lumen 26 in the cannula 20 and to exit the distal end 24 of the cannula 20 either through the outlet 28 (FIG. 2) or the filter outlet 29 (FIG. 3), into the vessel (not shown in FIGS. 2 and 3). The expansion frame 72 may open automatically, or may be mechanically expanded to its enlarged condition, thereby opening the filter mesh 80 substantially across the vessel and capturing any embolic material traveling therethrough. At any time, the expansion frame 72 may be closed to its contracted condition, entrapping any embolic material captured by the mesh 80, and the expandable filter 70 withdrawn by pulling proximally on the shaft 62. The expandable filter 70 may be returned into the cartridge 42, which may then be removed from the side port 32. A new modular filter cartridge 40 may be inserted into the side port 32 at any time thereafter, allowing a new expandable filter 70 to be introduced into the vessel, as desired during a surgical procedure.

The modular filter device and delivery system in accordance with the present invention is particularly useful in cardiac surgery. A cannula with modular filter as described above may be deployed within the aorta, for example, upstream of the carotid arteries. The aorta may be clamped upstream of the cannula with modular filter in preparation for a bypass procedure. This clamping generally substantially increases the risk of embolic deposits breaking loose from the wall of the aorta and traveling downstream. With the filter deployed, however, embolic material dislodged during this action may be captured by the filter device. Once the aorta is clamped, the risk of further embolic material being dislodged may be substantially reduced, and so the filter may be removed without substantial concern about embolic material escaping and possibly injuring the patient.

Later in the surgery, a new filter device may be introduced through the cannula into the aorta prior to any action which may substantially increase the risk of further embolic material breaking loose, such as when the aorta is unclamped. Because a new filter may be deployed, any embolic material that is dislodged may be captured more effectively, as opposed to a filter which must remain in the aorta throughout the procedure which may become clogged and impair blood flow through the vessel.

Similarly, the cannula with modular filter may be used to capture embolic material when balloon occlusion is used instead of clamping to close the aorta in bypass procedures. In this procedure, the occlusion balloon may be provided on the same cannula providing the modular filter. Alternatively, a catheter may be introduced into the aorta upstream of the bypass cannula, possibly through a cardioplegic cannula. A filter may be deployed prior to inflation of the occlusion balloon, thereby capturing any embolic material released by the balloon as it engages the walls of the aorta. This procedure may be slightly disfavored, however, since it may reduce the work space available for the bypass cannula and modular filter device.

An important feature of the present invention is that the filter may be placed immediately downstream of the location which is likely to generate emboli within the bloodstream, such as within the aorta. In addition, a filter device in accordance with the present may more effectively capture embolic material, because the expansion frame in the enlarged substantially engages the wall of the vessel extending the mesh across the vessel, and because the expansion frame may be closed before removal, entrapping the captured material. Thus, the arterial cannula with modular filter device in accordance with the present invention may more effectively capture and remove embolic material released during extended procedures, such as coronary bypass surgery, without clogging the filter and impairing blood flow through the vessel.

In some cases, it may desirable to provide the filter upstream of the cannula outlet through a separate filter outlet, as shown in FIG. 3. For example, this embodiment eliminates filtering the bypass blood which may accelerate clogging of the filter. It also may allow a variety of nozzle designs to be provided on the cannula, without concern that the outlet may be partially obstructed by the shaft of the filter device, as may occur with filters deployed through the cannula outlet.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A method of protecting a patient, comprising the steps of:
   introducing a tubular member into the patient's vessel, the tubular member having a lumen that extends from a proximal end to a distal end;
   inserting a filter into the proximal end of the tubular member;
   advancing the filter through the lumen into the vessel;
   deploying the filter;
   removing the filter from the vessel;
   removing the filter from the tubular member; and
   inserting a second filter into the tubular member after the step of removing the filter wherein embolic material is generated and filtered before the filter is removed from the vessel.

2. The method of claim 1, wherein the tubular member is fixed to an outer surface of a cannula.

3. The method of claim 2, wherein the cannula has a proximal end adapted to receive blood from a bypass-oxygenator machine.

4. The method of claim 1, wherein the filter comprises:
   a shaft having a proximal end and a distal end;
   an expansion frame mounted on the distal end of the shaft which is expandable between a contracted and enlarged condition; and
   a filter mesh attached to the expansion frame.

5. The method of claim 1, wherein the tubular member provides a hemostatic seal between the filter and the lumen.

6. The method of claim 1, wherein the expansion frame comprises a substantially circular belt of self-expanding material.

7. The method of claim 1, wherein the tubular member further comprises a suture flange.

8. The method of claim 2, wherein the lumen of the tubular member is separate from a lumen of the cannula.

9. The method of claim 1, wherein the vessel is an artery.

10. The method of claim 9, wherein the artery is an aorta.

11. A method of performing surgery on a patient, comprising the steps of:
    introducing a tubular member into the patient's artery, the tubular member having a lumen that extends from a proximal end to a distal end, wherein the tubular member is fixed to an outer surface of a cannula;
    inserting a first medical device into the proximal end of the tubular member;
    advancing the first medical device through the lumen into the artery;
    deploying the first medical device; removing the first medical device from the artery; and
    inserting a second medical device into the tubular member after the step of removing the first medical device.

12. The method of claim 11, wherein the medical device is a filter.

13. The method of claim 11, wherein the lumen of the tubular member merges and communicates with a lumen of the cannula.

14. The method of claim 11, wherein the lumen of the tubular member is separate from a lumen of the cannula.

15. The method of claim 11, wherein the artery is the patient's aorta.

* * * * *